US00PP14870P2

(12) United States Plant Patent
Hooijman

(10) Patent No.: US PP14,870 P2
(45) Date of Patent: Jun. 8, 2004

(54) HYPERICUM PLANT NAMED 'ESMGRAPE'

(50) Latin Name: *Hypericum androsaemum*
Varietal Denomination: Esmgrape

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 10/637,052

(22) Filed: Aug. 7, 2003

(51) Int. Cl.[7] ..... A01H 5/00
(52) U.S. Cl. ..... Plt./226
(58) Field of Search ..... Plt./226, 263

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Hypericum plant named 'Esmgrape', characterized by its upright plant habit; dark green-colored leaves; large green-colored fruits; and good postproduction longevity.

2 Drawing Sheets

Botanical classification/cultivar designation: *Hypericum androsaemum* cultivar Esmgrape.

BACKGROUND OF THE INVENTION

The present Invention relates to a new and distinct cultivar of Hypericum plant, botanically known as *Hypericum androsaemum,* commercially used as cut stems with fruits, and hereinafter referred to by the name 'Esmgrape'.

The new Hypericum is a product of a planned breeding program conducted by the Inventor in El Quinche, Pichincha, Ecuador. The objective of the breeding program was to develop cut Hypericum varieties with attractive fruit coloration.

The new cultivar originated from a cross-pollination made by the Inventor in November, 1999 of a proprietary selection of *Hypericum androsaemum* identified as Code 68, not patented, as the female, or seed, parent with an unidentified selection of *Hypericum androsaemum,* not patented, as the male, or pollen, parent. The cultivar Esmgrape was discovered and selected by the Inventor as a flowering plant within the progeny of the stated cross-pollination in a controlled environment in El Quinche, Pichincha, Ecuador.

Asexual reproduction of the new Hypericum by terminal cuttings taken at El Quinche, Pichincha, Ecuador since August, 2000, has shown that the unique features of this new Hypericum are stable and reproduced true to type in successive generations of asexual reproduction.

SUMMARY OF THE INVENTION

The following traits have been repeatedly observed and are determined to be the unique characteristics of 'Esmgrape'. These characteristics in combination distinguish 'Esmgrape' as a new and distinct cultivar:

1. Upright plant habit.
2. Dark green-colored leaves.
3. Large green-colored and rounded fruits.
4. Good postproduction longevity.

Plants of the new Hypericum differ from plants of the female parent selection identified as Code 68 in the following characteristics:

1. Plants of the new Hypericum are not as erect as plants of the female parent selection.
2. Plants of the new Hypericum have larger fruits than plants of the female parent selection.
3. Plants of the new Hypericum and the female parent selection differ in fruit coloration.

Plants of the new Hypericum differ from plants of the male parent selection primarily in fruit size and coloration.

Plants of the new Hypericum can be compared to plants of the Hypericum cultivar Bosapin, disclosed in U.S. Plant Pat. No. 10,993. In side-by-side comparisons conducted in El Quinche, Pichincha, Ecuador, plants of the new Hypericum differed from plants of the cultivar Bosapin in the following characteristics:

1. Plants of the new Hypericum were not as erect as plants of the cultivar Bosapin.
2. Plants of the new Hypericum had more rounded fruits than plants of the cultivar Bosapin.
3. Plants of the new Hypericum and the cultivar Bosapin differed in fruit coloration.

BRIEF DESCRIPTION OF THE PHOTOGRAPHS

The accompanying colored photographs illustrate the overall appearance of the new Hypericum, showing the colors as true as it is reasonably possible to obtain in colored reproductions of this type. Colors in the photographs may differ slightly from the color values cited in the detailed botanical description which accurately describe the colors of the new Hypericum.

The photograph on the first sheet comprises a side perspective view of a typical stem of 'Esmgrape' in fruit.

The photograph on the second sheet is a close-up view of a typical cluster of fruits, the upper surface of a typical leaf, and the lower surface of a typical leaf of 'Esmgrape'.

DETAILED BOTANICAL DESCRIPTION

The new Hypericum has not been observed under all possible environmental conditions. The phenotype may vary somewhat with variations in environment such as temperature, daylength and light intensity, without, however, any variance in genotype.

The aforementioned photographs, following observations and measurements describe plants grown in El Quinche, Pichincha, Ecuador, in an outdoor nursery and under commercial production practices. Plants were about one year old. During the production of the plants, day temperatures ranged from 12 to 30° C. and day temperatures ranged from 5 to 12° C. Plants were pinched about two weeks after planting. In the following description, color references are made to The Royal Horticultural Society Colour Chart, 2001 Edition, except where general terms of ordinary dictionary significance are used.

Botanical classification: *Hypericum androsaemum* cultivar Esmgrape.

Parentage:

*Female parent.*—Proprietary selection of *Hypericum androsaemum* identified as Code 68, not patented.

*Male parent.*—Unidentified selection of *Hypericum androsaemum,* not patented.

Propagation:

*Type.*—Terminal cuttings.

*Time to initiate roots.*—About 7 to 10 days at 22 to 30° C.

*Time to produce a rooted cutting.*—About 28 to 35 days at 22 to 30° C.

*Root description.*—Fibrous, fine; color, N167B.

*Rooting habit.*—Freely branching, dense.

Plant description:

*Plant form.*—Upright and somewhat outwardly spreading perennial woody shrub; erect inverted triangle.

*Growth habit.*—Moderately vigorous. Freely basal branching; dense and bushy growth habit.

*Plant height.*—About 90.2 cm.

*Plant width* (*spread*).—About 35 cm.

*Quantity of stems per year.*—About 5; production of stems increases with age of plants.

*Lateral branches.*—Length: About 88 cm. Diameter: About 5 mm. Internode length: About 4.6 cm. Strength: Moderately strong to strong. Texture: Smooth; glabrous. Color: 142B overlain with 175A.

*Foliage description.*—Arrangement: Opposite, simple; sessile. Length: About 6.8 cm. Width: About 4.7 cm. Shape: Cordate. Apex: Acute to retuse. Base: Cordate. Margin: Entire. Texture, upper and lower surfaces: Glabrous; smooth. Venation pattern: Pinnate. Color: Developing leaves, upper surface: 137A. Developing leaves, lower surface: 139C. Fully expanded leaves, upper surface: 139A. Fully expanded leaves, lower surface: 139C. Venation, upper surface: 145A. Venation, lower surface: 143A.

Flower description:

*Flower type and habit.*—Single flowers arranged in terminal compound umbels with about 22 flowers per lateral branch. Flowers fragrant. Flowers not persistent. Flowers face upright.

*Natural flowering season.*—Summer, typically July through early September in The Netherlands; flowering period typically lasts about 60 days.

*Postproduction longevity.*—Cut stems are typically harvested when all flowers have developed fruits. Flowers last about three days on the plant. Postproduction longevity of cut stems with fruits about 14 to 18 days.

*Inflorescence height.*—About 15 cm.

*Inflorescence diameter.*—About 16 cm.

*Flower buds.*—Height: About 1 cm. Diameter: About 7 mm. Shape: Ovoid. Color: Towards the apex, 14B; towards the base, 1B.

*Flowers.*—Diameter: About 2.6 cm. Depth: About 1.4 cm.

*Petals.*—Quantity per flower: Typically five. Length: About 1.1 cm. Width: About 8 mm. Shape: Oval. Aspect: Incurved. Apex: Obtuse. Base: Attenuate. Margin: Entire. Texture, upper and lower surfaces: Smooth, glabrous. Color: Developing and fully expanded petals, upper surface: 13A. Developing and fully expanded petals, lower surface: 10A.

*Sepals.*—Quantity per flower: Typically five. Length: About 1.1 cm. Width: About 9 mm. Shape: Ovate. Apex: Obtuse. Base: Rounded. Margin: Entire. Texture, upper and lower surfaces: Smooth, glabrous. Color: Developing sepals, upper surface: 141B. Developing sepals, lower surface: 139C; towards the apex, overlain with 60B. Fully developed sepals, upper surface: 141A. Fully developed sepals, lower surface: 139C.

*Peduncles.*—Length: About 4.6 cm. Diameter: About 3 mm. Orientation: Erect to about 40° from vertical. Strength: Strong to moderately strong. Color: 145A overlain with 176B.

*Pedicels.*—Length: About 1 cm. Diameter: About 2 mm. Orientation: Erect to about 40° from vertical. Strength: Moderately strong. Color: 145A overlain with 176B.

*Reproductive organs.*—Stamens: Quantity per flower: About 100. Anther shape: Reniform. Anther length: About 0.8 mm. Anther color: 16A. Pollen amount: Scarce. Pollen color: 16A to 21A. Pistils: Quantity per flower: Typically three. Pistil length: About 1 cm. Stigma shape: Globular. Stigma color: 63B. Style length: About 4.3 mm. Style color: 1B. Ovary color: 1B.

*Fruits.*—Quantity per flower: One. Days to ripening: About 52 to 56. Type: Capsule. Shape: Ellipsoidal. Length: About 1.1 cm. Diameter: About 1 cm. Texture: Smooth, glabrous. Color: N144C.

*Seeds.*—Length: About 0.1 mm. Diameter: About 0.03 mm. Texture: Smooth, glabrous. Color: 200C.

Disease/pest resistance: Plants of the new Hypericum have not been observed to be resistant to pathogens and pests common to Hypericum.

Temperature tolerance: Plants of the new Hypericum have been observed to tolerate temperatures ranging from 0 to 30° C.

It is claimed:

1. A new and distinct cultivar of Hypericum plant named 'Esmgrape', as illustrated and described.

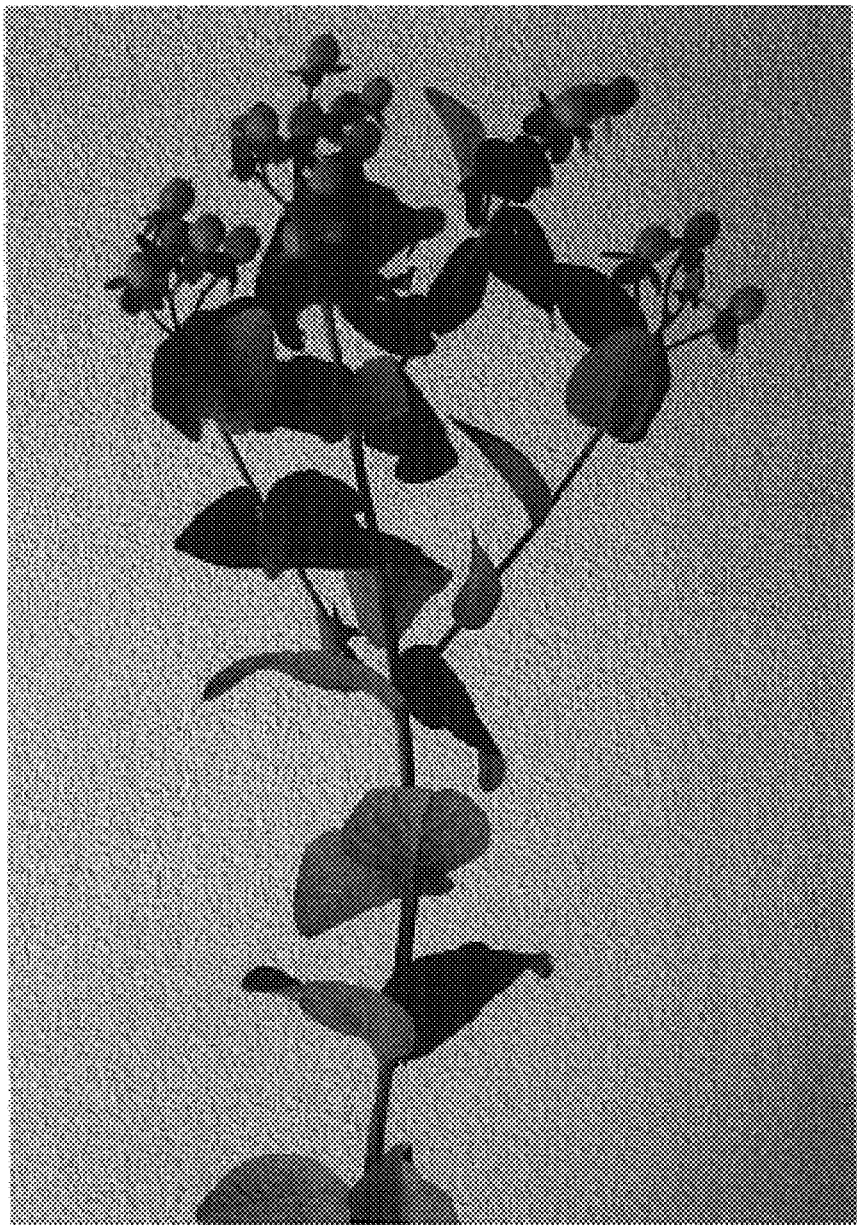

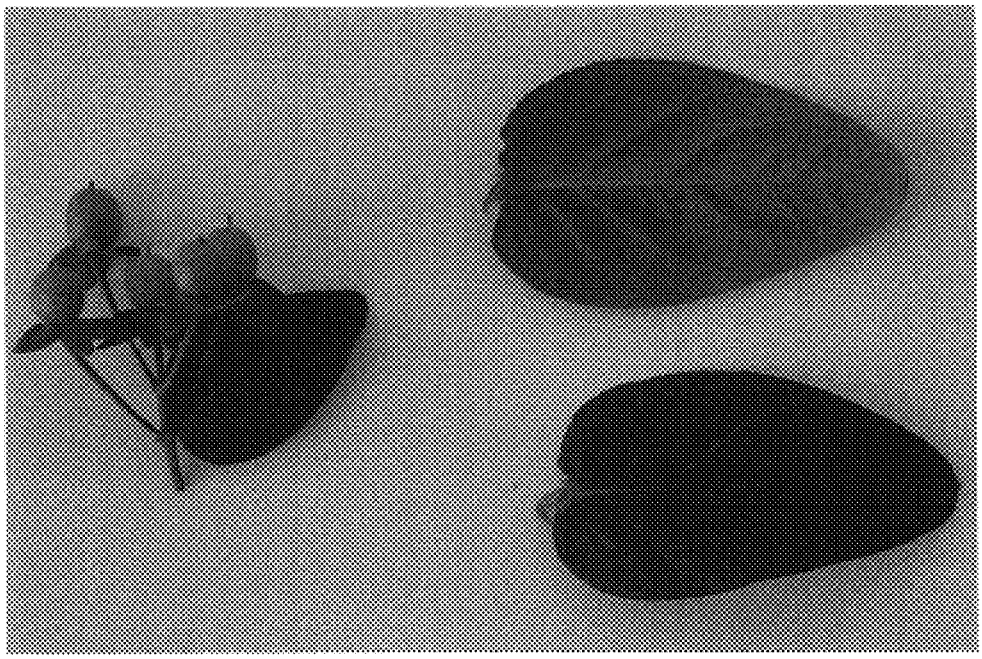

* * * * *